(12) United States Patent
Gostelow

(10) Patent No.: US 7,305,989 B2
(45) Date of Patent: Dec. 11, 2007

(54) MEDICO-SURGICAL INSTRUMENTS

(75) Inventor: Thomas Gostelow, Chester (GB)

(73) Assignee: Smiths Group PLC, London (GB)

( * ) Notice: Subject to any disclaimer, the term of this patent is extended or adjusted under 35 U.S.C. 154(b) by 575 days.

(21) Appl. No.: 10/643,939

(22) Filed: Aug. 20, 2003

(65) Prior Publication Data

US 2004/0035432 A1 Feb. 26, 2004

(30) Foreign Application Priority Data

Aug. 24, 2002 (GB) .................................. 0219773.9
Mar. 25, 2003 (GB) .................................. 0306799.8

(51) Int. Cl.
*A61M 16/00* (2006.01)
*A61B 19/00* (2006.01)

(52) U.S. Cl. ...................... 128/207.14; 128/207.29; 128/200.26; 128/898

(58) Field of Classification Search .......... 128/200.24, 128/200.26, 205.23, 207.14, 207.15, 207.16, 128/207.17, 207.18, 207.29, 898; 606/185; 324/300–322

See application file for complete search history.

(56) References Cited

U.S. PATENT DOCUMENTS

| 2,623,521 A | | 12/1952 | Shaw | |
| 3,688,773 A | | 9/1972 | Weiss | |
| 4,364,391 A | * | 12/1982 | Toye | 128/207.29 |
| 4,471,778 A | * | 9/1984 | Toye | 128/207.29 |
| 4,898,163 A | * | 2/1990 | George | 128/200.26 |
| 4,978,334 A | * | 12/1990 | Toye et al. | 604/506 |
| 5,423,760 A | * | 6/1995 | Yoon | 604/164.11 |
| 5,507,279 A | * | 4/1996 | Fortune et al. | 128/200.26 |
| 6,109,264 A | * | 8/2000 | Sauer | 128/207.29 |
| 6,382,209 B1 | * | 5/2002 | Toye | 128/207.14 |

FOREIGN PATENT DOCUMENTS

| EP | 0407663 | 1/1991 |
| EP | 1 092 448 | 1/2002 |
| GB | 2 225 953 | 6/1990 |

\* cited by examiner

*Primary Examiner*—Justine R. Yu
*Assistant Examiner*—Annette Dixon
(74) *Attorney, Agent, or Firm*—Louis Woo

(57) ABSTRACT

An instrument for providing ventilation access to the trachea has a hollow needle with a sharp tip, a tube extending within the needle and a spring urging the tube to project a short distance from the patient end of the needle. The rear end of the tube carries two colored flags one of which is visible at a time in a transparent window towards the machine end of the needle. When the patient end of the instrument is pushed through neck tissue overlying the trachea the inner tube is pushed rearwardly so that a flag of one color is visible. When the patient end of the instrument enters the trachea the spring can push the inner tube forwardly so that the other flag is visible. In one embodiment the instrument carries a dilator and tracheostomy tube that can be slid off the needle after penetration. In another embodiment, ventilation equipment is connected to the rear of the inner tube and the patient is ventilated through the instrument itself.

14 Claims, 2 Drawing Sheets

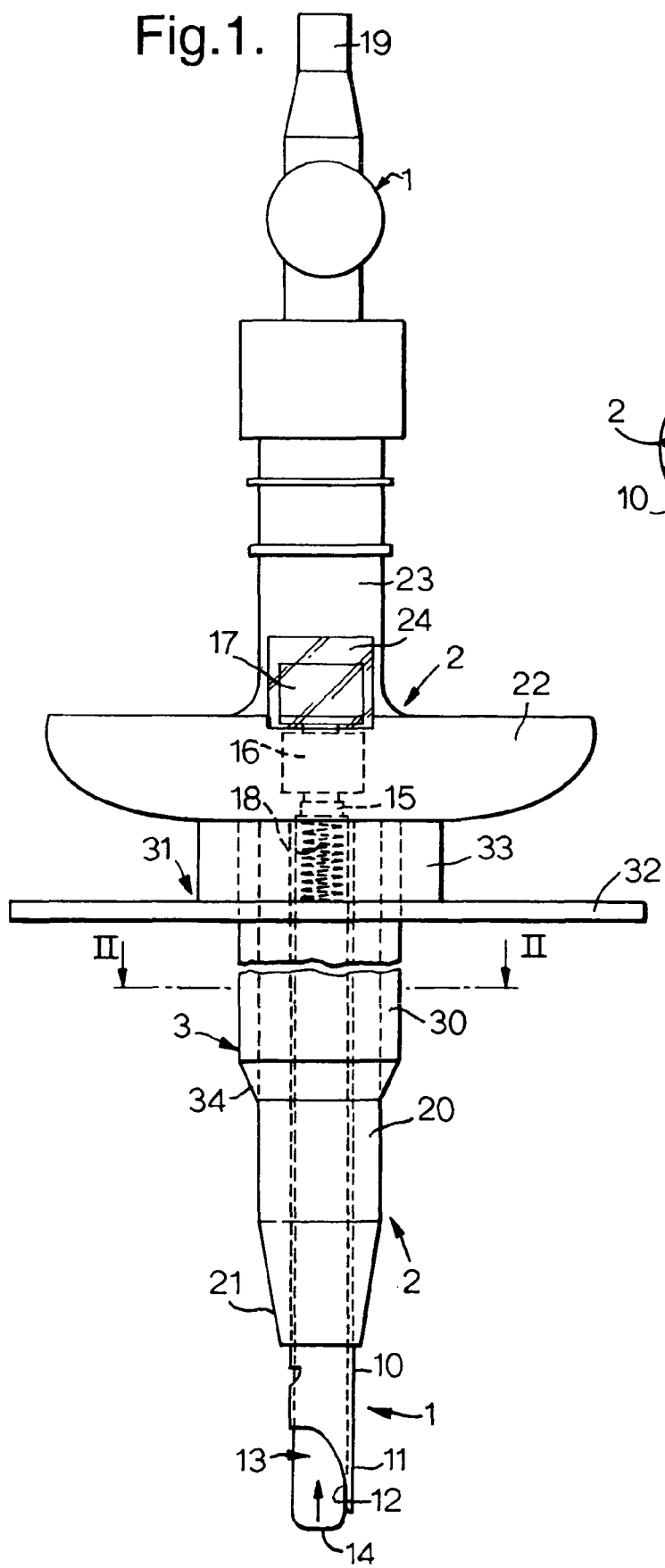
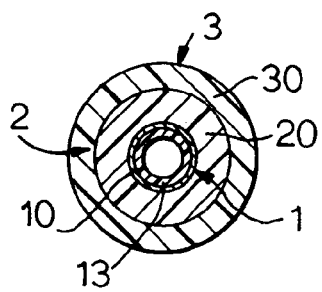

MEDICO-SURGICAL INSTRUMENTS

BACKGROUND OF THE INVENTION

This invention relates to medico-surgical instruments.

Various procedures and instruments are used to ventilate patients via the trachea. Tracheostomies can be made by a conventional surgical technique or by a percutaneous technique, which is quicker and more suited to emergency situations. In the usual percutaneous technique a needle is pushed through the skin of the throat into the trachea. Entry of the needle to the trachea is detected by a loss-of-resistance technique involving a syringe filled with air connected to the needle hub. The tip of the needle is blocked while it is passing through the neck tissue so that manual pressure applied to the needle plunger encounters a resistance to movement. When the tip of the needle enters the trachea air can flow and the plunger can move forwardly, enabling entry to be detected. The syringe is then removed and a guidewire is slid along the needle. The needle is then pulled out along the guidewire, leaving the guidewire in position. The opening into the trachea is then enlarged by sliding a dilator or a series of dilators of increasing size along the guidewire into the trachea. When the opening has been enlarged sufficiently, a tracheostomy tube is slid along the guidewire, following which the guidewire can be removed. Although the apparatus involved in this technique has been used successfully for many years, the number of different components and steps is not ideal for adverse situations, such as at the site of a trauma incident, and it may not be suitable for less experienced clinicians or paramedics.

An alternative technique used in emergency situations is percutaneous transtracheal ventilation. In this technique a sharp-tipped needle penetrates the trachea and the external, machine end of the needle is connected to a jet ventilation machine so that breathing gas is supplied to the trachea via the needle, which is left in position. This arrangement can be used to provide emergency ventilation for up to about one hour, which is usually sufficient time for the patient to be provided with alternative ventilation. The advantage of this procedure is that it can be carried out relatively easily by ambulance crew and paramedics and it does not involve the need for cutting with a scalpel. The procedure does, however, have several disadvantages. First, there is a risk that the needle will not be inserted to the correct depth, because of variations in thickness of neck tissue overlying the trachea. If the needle is not inserted far enough its tip may be located in the anterior tissues surrounding the trachea instead of in the trachea itself. If inserted too far, the needle may damage the posterior wall of the trachea. Second, because the ventilation gas emerges through the open tip of the needle and the bore of the needle is relatively small compared with a tracheal tube, the gas emerges as a jet directed longitudinally of the needle and towards the posterior wall of the trachea. Where the gas jet impinges on the tissue of the trachea it may cause drying and necrosis.

Another problem with emergency ventilation instruments is that it is usually necessary to hyperextend the neck in order to provide access to the trachea. Where the patient has suffered neck injury, or is suspected of having suffered a neck injury it is important that there is minimal movement of the neck. This is a particular disadvantage because patients requiring emergency ventilation are often those that have been involved in an accident of the kind that can cause neck injury.

BRIEF SUMMARY OF THE INVENTION

It is an object of the present invention to provide alternative medico-surgical instruments for ventilating a patient via the trachea.

According to one aspect of the present invention there is provided a medico-surgical instrument for ventilation via the trachea comprising a hollow needle having a sharp tip adapted to penetrate the trachea through neck tissue, an elongate inner member located within the needle such that the member can slide along its length relative to the needle, means for urging the inner member forwardly resiliently relative to the needle, such that the forward end of the inner member is located forwardly of the needle tip before use but is displaced rearwardly during passage through the neck tissue by engagement with the tissue and moves forwardly relative to the needle when the trachea is penetrated, and indicator means towards the rear end of the needle for indicating the position of the elongate member relative to the needle so that the user knows that the trachea has been penetrated.

The instrument may include a tracheostomy tube extending along the outside of the needle so that the needle can be removed to leave the tracheostomy tube in the trachea after penetration of the trachea. The instrument may include a dilator with a tapered patient end mounted on the needle, the tracheostomy tube being mounted on the outside of the dilator with the tapered end of the dilator projecting from the patient end of the tracheostomy tube. The tracheostomy tube is preferably helically reinforced and may be cuffed. The inner member may be hollow and provide a gas passage along the member. The inner member may be closed at its patient end and open through a side opening adjacent the patient end. The inner member preferably opens through two side openings adjacent the patient end and the or each side opening may be longitudinally elongated. The instrument may include a coupling towards the machine end of the inner member by which gas can be supplied to the inner member. The indicator preferably includes a visual indicator, which may include a colored flag movable behind a transparent window.

According to another aspect of the present invention there is provided apparatus for ventilating via the trachea including a hollow needle having a sharp tip adapted to penetrate the trachea through neck tissue, an inner, elongate, hollow member opening towards its patient end and slidably mounted within the needle, means urging the inner member forwardly relative to the needle, such that a forward end of the inner member is located forwardly of the needle tip before use but is displaced rearwardly during passage through neck tissue by engagement with the tissue and moves forwardly relative to the needle when the trachea is penetrated, an indicator towards the rear end of the needle for indicating position of the elongate member relative to the needle so that the user knows that the trachea has been penetrated, and ventilation equipment connected with the rear end of the elongate inner member by which ventilation gas is supplied to the trachea via the inner member.

Instruments according to the present invention will now be described, by way of example, with reference to the accompanying drawings.

BRIEF DESCRIPTION OF THE DRAWINGS

FIG. 1 is a side elevation view of an instrument in the form of tracheostomy apparatus;

FIG. 2 is a cross section along the line II-II of FIG. 1;

DETAILED DESCRIPTION OF THE PREFERRED EMBODIMENTS

Figures 3, 4:
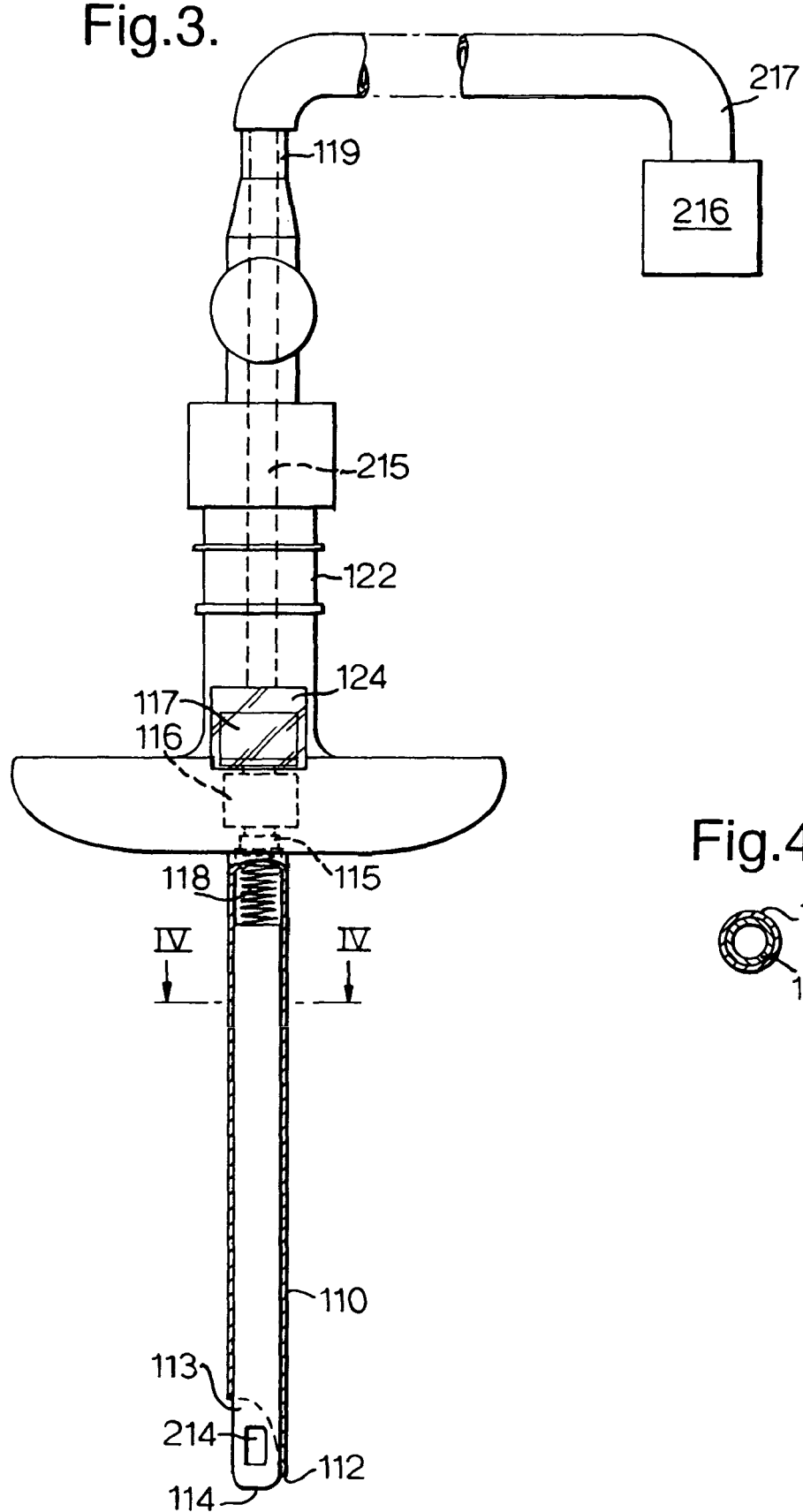
FIG. 3 is a side elevation view of an alternative ventilation instrument.
FIG. 4 is a cross section along the line IV-IV of FIG. 3.

With reference first to FIGS. 1 and 2, the tracheostomy apparatus comprises a needle assembly 1, a dilator assembly 2 mounted on the outside of the needle assembly and a tracheostomy tube 3 mounted on the outside of the dilator assembly. These components are supplied mounted with one another and are used with one another during the initial stage of the tracheostomy procedure.

The needle assembly 1 is similar to a Veress needle used in chest surgery and laparascopy. The assembly 1 has a straight, rigid steel needle 10 of circular section which opens axially at its patient end 11 through a cutting tip 12. An inner elongate member in the form of a hollow tube 13 extends along the needle 10 as a sliding fit. The tube 13 may be of a rigid plastics material and has a rounded, open forward or patient end 14. The rear end 15 of the tube 13 projects from the needle 10 and carries an indicator in the form of two colored flags 16 and 17 spaced axially of one another. The forward flag 16 is red; the rear flag 17 is green. The assembly 1 also includes a helical spring 18 mounted between the needle 10 and the tube 13, urging the tube forwardly relative to the needle. The force of the spring 18 is sufficient to push the tube 13 forwardly against friction with the inside of the needle 10 and to overcome obstructions caused by tissue fragments or fluid at the tip of the needle. The force of the spring 18, however, is not sufficient to prevent the tube 13 being pushed rearwardly relative to the needle 10 when this is pushed against patient tissue. The rear end 19 of the needle assembly 1 projects at the rear of the tracheostomy assembly and the needle assembly can be withdrawn rearwardly from the tracheostomy assembly by pulling on the rear end. The passage through the inner tube 13 opens through the rear end of the needle assembly 1.

The dilator assembly 2 comprises a shaft 20 of a plastics material with a tapered forward end 21. The shaft 20 is a close sliding fit on the needle assembly 1 with its forward end being located about 10 mm to the rear of the patient end 11 of the needle 10. The natural shape of the dilator assembly 2 is curved but, while mounted on the needle assembly 1, it is maintained straight by the straight shape of the needle assembly. At its rear end, the dilator assembly 2 has a handle 22 and a hub 23 in which the rear end 19 of the needle assembly 1 is received. The hub 23 has a transparent window 24 in one side located in alignment with the flags 16 and 17 on the inner tube 13. The position of the window 24 is such that, when the inner tube 13 is in its natural, forwards position relative to the needle 10, the rear, green flag 17 is visible through the window and the forward, red flag 16 is not visible. When the inner tube 13 is pushed rearwardly, the red flag 16 becomes visible in the window 24 in place of the green flag 17.

The tracheostomy tube 3 may be of conventional construction, comprising a flexible, helically-reinforced shaft 30, which is naturally curved but is held straight when mounted on the needle assembly 1. At its rear end 31 the tube 3 has a neck flange 32 and a standard 15 mm hub or female connector 33. The tube 3 is a close sliding fit on the dilator assembly 2 with its forward, patient end 34 spaced from the forward end 21 of the dilator by about 20 mm. The shaft 30 may have an inflatable sealing cuff (not shown) of the usual kind close to its patient end 34. The rear end of the dilator assembly 2 is received in the connector 33.

The tracheostomy assembly is provided as shown in FIGS. 1 and 2 with the tracheostomy tube 3 loaded on the dilator assembly 2 and with the dilator assembly loaded on the needle assembly 1. Initially, therefore, the assembly is straight, the needle assembly 1 projects from its patient end and the green flag 17 is visible. To make a tracheostomy, the cutting tip 12 of the needle assembly 1 is brought up to the skin of the throat over the trachea, usually in the cricothyroid region, with the assembly generally orthogonal to the skin surface. As pressure is applied, the inner tube 13 is pushed rearwardly by the skin surface and the red flag 16 becomes visible in the window 24. Further pressure causes the tip 12 of needle 1 to penetrate the skin and underlying tissue. The needle 10 enters the neck tissue followed by the forward, tapered end 21 of the dilator 2. When the tip 12 of the needle 1 enters the trachea, its open end 11 is no longer occluded by tissue so the spring 18 can move the inner tube 13 to its forward position, causing the green flag 17 to be visible. This provides an indication to the clinician that the trachea has been entered. When the needle 10 enters the trachea a gas passage is provided into the trachea via the passage through the inner tube 13. If the tracheostomy assembly should be inserted too far, so that it contacts the posterior wall of the trachea, this will push back the inner tube 13 and cause the red flag 16 to appear as a warning to the clinician. This warning flag 16 will also appear if the tip 12 of the assembly should contact an obstruction within the trachea.

The clinician then angles the assembly so that the tip 12 points down the trachea, that is, towards the patient's feet. He then continues to push in the assembly until the tip 34 of the tracheostomy tube 3 is adjacent the skin surface, at which point the tip 21 of the dilator 2 should be located in the trachea. He then pulls out the needle assembly 1 by gripping its rear end 19 while holding the handle 22 so that the dilator 2 is not pulled out. After the needle assembly 1 has been removed he continues to push in the assembly of the dilator 2 and the tracheostomy tube 3. The taper 21 on the dilator 2 enlarges the opening through the neck tissue sufficiently for the tracheostomy tube 3 to be pushed in. As the dilator 2 emerges into the trachea it bends to its natural shape pointing down the trachea. This helps guide the tracheostomy tube 3, which also bends as it is inserted. Once the tracheostomy tube 3 has been fully inserted, with its flange 32 abutting the skin surface, the dilator 2 is removed and the cuff on the tracheostomy tube is inflated to seal with the trachea.

The instrument of the present invention provides a clear indication of entry into the trachea without the need to use a loss-of-resistance syringe. It also provides an indication of contact with the posterior wall. The apparatus can be provided ready assembled for immediate use making it ideally suited for emergency applications. The apparatus is easy to use making it safe for use by less skilled people.

The instrument could be modified in various ways. For example, the elongate member extending along the bore of the needle need not be a tube but could be a rod or the like. Instead of a visual indicator, the indicator could provide an audible indication such as by completing an electrical circuit on sliding forwards or rearwards.

The instrument need not have a tracheostomy tube and dilator but could be used itself to provide ventilation in the manner shown in FIGS. 3 and 4. Components of the instrument equivalent to those of the instrument shown in FIGS. 1 and 2 are given the same reference numeral with the addition of 100.

The instrument has a needle 110 assembly with an inner hollow tube 113 that differs from the tube 13 in that its patient end 114 is closed, the needle opening through two longitudinally-elongated side openings 214 located diametrically opposite one another close to the tip. The rear end 115 of the tube 113 projects from the needle 110, is open and communicates with a bore 215 extending rearwardly along a handle 122

The rear end 115 of the inner tube 113 also carries two colored flags 116 and 117, which are movable behind a transparent window 124 in the handle 122. The handle 122 terminates at its rear, machine end in a male coupling 119 through which opens the bore 215. Jet ventilation equipment 216 is connected to the connection 119, and hence to the inner tube 113 by tubing 217.

The instrument does not carry a tracheostomy tube or dilator as does the instrument shown in FIGS. 1 and 2.

The instrument is used initially in the same manner as the instrument shown in FIGS. 1 and 2 to provide access to the trachea, usually in the cricothyroid region. During insertion the red flag 116 becomes visible in the window 124 until the trachea is penetrated when the green flag 117 become visible.

When the tip 112 of the needle 110 is correctly located in the trachea, the openings 214 in the inner tube 113 are exposed and breathing gas can be supplied to the instrument from the ventilation equipment 216 emerging into the trachea via the openings in the inner tube. The instrument remains in place while ventilation takes place and is not removed as with the instrument shown in FIGS. 1 and 2.

The instrument is easy to use making it safe for use by less skilled people. Because the gas emerges from side openings there is less risk of tracheal tissue being damaged by exposure to a gas jet. Another advantage of the instrument is that it enables ventilation without having to hyperextend the neck so that it lends itself particularly for use with patients having a neck injury or a suspected neck injury.

The instrument could have an adjustable flange, such as of the kind described in GB 2227941, to enable it to be secured to the neck after insertion.

It is not essential that the inner tube open through side apertures since it could open through its end, although this would give rise to jetting problems. These problems might be reduced by having side apertures in addition to an open end so that some of the gas pressure is dissipated by lateral flow from the side apertures. Where side apertures are used, the instrument could be arranged so that the side apertures are totally blocked by the needle when the inner tubular member is in its retracted position. In this way, gas could be supplied to the instrument continuously but would be prevented from emerging at the patient end of the instrument during passage through neck tissue, and would automatically emerge into the trachea when the trachea is penetrated.

What I claim is:

1. A medico-surgical instrument for ventilation via the trachea comprising: a hollow needle having a sharp tip adapted to penetrate the trachea through neck tissue; an elongate inner member located within said needle such that the member can slide along its length relative to the needle; a resilient member adapted to urge said inner member forwardly relative to said needle, such that a forward end of said inner member is located forwardly of said needle tip before use but is displaced rearwardly during passage through neck tissue by engagement with the tissue and moves forwardly relative to said needle when said trachea is penetrated; a tracheostomy tube removably supported by and extending along the outside of said needle: and an indicator towards a rear end of said needle for indicating position of said elongate member relative to said needle such that said needle can be removed to leave the tracheostomy tube in position extending through neck tissue when said indicator indicates that the trachea has been penetrated.

2. An instrument according to claim 1 including a dilator with a tapered patient end mounted on said needle, and wherein said tracheostomy tube is mounted on an outside of the dilator with the tapered end of the dilator projecting from a patient end of said tracheostomy tube.

3. An instrument according to claim 1, wherein said tracheostomy tube is helically reinforced.

4. An instrument according to claim 1, wherein said tracheostomy tube is cuffed.

5. An instrument according to claim 1, wherein said inner member is hollow and provides a gas passage along said member.

6. An instrument according to claim 5, wherein said inner member is closed at its patient end and opens through a side opening adjacent the patient end.

7. An instrument according to claim 6, wherein said inner member opens through two side openings adjacent the patient end.

8. An instrument according to claim 6, wherein said side opening is longitudinally elongated.

9. An instrument according to claim 5 including a coupling towards a machine end of said inner member by which gas can be supplied to said inner member.

10. An instrument according to claim 1, wherein said indicator means includes a visual indicator.

11. An instrument according to claim 10, wherein said visual indicator includes a colored flag movable behind a transparent window.

12. A tracheostomy instrument for ventilation via the trachea comprising: a hollow needle having a sharp tip adapted to penetrate the trachea through neck tissue; an elongate inner member located within said needle such that the member can slide along its length relative to the needle; a spring between said needle and said inner member urging said inner member forwardly relative to said needle, such that a forward end of said inner member is located forwardly of said needle tip before use but is displaced rearwardly during passage through neck tissue by engagement with the tissue and moves forwardly relative to said needle when said trachea is penetrated; a visual indicator towards a rear end of said needle for indicating position of said elongate member relative to said needle so that the user knows that the trachea has been penetrated; a dilator mounted on said needle; and a tracheostomy tube removably mounted on said dilator such that a patient end of said dilator extends beyond a patient end of said tracheostomy tube and such that said dilator and tracheostomy tube can be slid off said needle when said indicator indicates that the trachea has been penetrated.

13. A method of inserting a tracheostomy tube into a patient's trachea comprising the steps of: providing said tracheostomy tube loaded on an instrument comprising a hollow needle having a sharp tip, an elongate member extending within the needle and projecting from a patient end of said needle and an indicator towards a machine end of the instrument for indicating movement of said elongate member relative to said needle; inserting a patient end of the instrument through neck tissue of a patient into the trachea until a change in the status of the indicator indicates that the trachea has been penetrated; and sliding said instrument rearwardly relative to said tracheostomy tube to remove said instrument and to position said tracheostomy tube in the trachea.

14. A method according to claim 13, wherein said tracheostomy tube is loaded on a dilator on said instrument and the method includes the step of advancing said dilator forwardly along said instrument to advance said tracheostomy tube into the trachea, and subsequently removing said dilator to leave said tracheostomy tube in position.

* * * * *